(12) United States Patent
Wijay

(10) Patent No.: US 6,203,569 B1
(45) Date of Patent: *Mar. 20, 2001

(54) FLEXIBLE STENT

(76) Inventor: Bandula Wijay, 1903 Carriage Creek Dr., Friendswood, TX (US) 77546

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/883,801

(22) Filed: Jun. 27, 1997

Related U.S. Application Data

(63) Continuation of application No. 08/582,657, filed on Jan. 4, 1996.

(51) Int. Cl.⁷ .................................................. A61F 2/06
(52) U.S. Cl. .................... 623/1.15; 623/1.16; 623/1.17
(58) Field of Search .................................... 623/1, 11, 12, 623/1.15, 1.16, 1.17

(56) References Cited

U.S. PATENT DOCUMENTS

| | | |
|---|---|---|
| Re. 34,037 | 8/1992 | Innue et al. |
| 4,503,569 | 3/1985 | Dotter |
| 4,580,568 | 4/1986 | Gianturco |
| 4,732,152 | 3/1988 | Wallsten et al. |
| 4,740,207 | 4/1988 | Kreamer |
| 4,776,337 | 10/1988 | Palmaz |
| 4,795,458 | 1/1989 | Regan |
| 4,820,298 | 4/1989 | Leveen et al. |
| 4,886,062 | 12/1989 | Wiktor |
| 4,913,141 | 4/1990 | Hillstead |
| 4,950,227 | 8/1990 | Savin et al. |
| 4,964,853 | 10/1990 | Sugiyama et al. |
| 4,969,458 | 11/1990 | Wiktor |
| 4,990,151 | 2/1991 | Wallsten |
| 5,100,429 | 3/1992 | Sinofsky et al. |

(List continued on next page.)

FOREIGN PATENT DOCUMENTS

| | | | |
|---|---|---|---|
| 90310775 | 10/1990 | (EP) | |
| 94302929 | 4/1994 | (EP) | |
| 94309839 | 12/1994 | (EP) | |
| 9113820 | * 11/1991 | (FR) | A61F/2/04 |

OTHER PUBLICATIONS

AngioStent Balloon Expandable Stent System, AngioDynamics Division of E–Z–EM, Inc., Sept., 1994 (brochure).
Gianturco–Roubin Flex–Stent Coronary Stents, Cook Cardiology, 1995 (brochure).
Medtronic Wiktor GX, Medtronic Interventional Vascular, no date (brochure).
Miscellaneous literature regarding PS stent, no date.
Miscellaneous literature regarding stent, no date.
Miscellaneous literature regarding Wiktor Stents, no date.
Miscellaneous literature regarding Wallstent, no date.
Doanld. S. Baim, MD, "New Stent Designs," 2 pages, dated after Aug., 1995.

*Primary Examiner*—David J. Isabella
*Assistant Examiner*—Choon P. Koh
(74) *Attorney, Agent, or Firm*—Duane, Morris & Heckscher LLP

(57) ABSTRACT

A stent is disclosed which comprises generally of ring having, in the preferred embodiment, crossties that have flexibility by having at least one bend. The rings themselves have predetermined stress-relieving points to predispose, by stress relief, particular segments of each ring to bend upon application of an expansion force such as by a balloon or by other means. In the preferred embodiment, the individual rings have notches, reducing the cross-sectional areas at particular locations adjacent reversing bends such that upon radial expansion, bending occurs at these reduced cross-sectional areas to prevent stress from accumulating at the reversing bends.

26 Claims, 4 Drawing Sheets

U.S. PATENT DOCUMENTS

| | | |
|---|---|---|
| 5,108,416 | 4/1992 | Ryan et al. . |
| 5,133,732 | 7/1992 | Wiktor . |
| 5,135,536 | 8/1992 | Hillstead . |
| 5,139,480 | 8/1992 | Hickle et al. . |
| 5,158,548 | 10/1992 | Lau et al. . |
| 5,160,341 | 11/1992 | Brenneman et al. . |
| 5,163,951 | 11/1992 | Pinchuk et al. . |
| 5,163,952 | 11/1992 | Froix . |
| 5,163,958 | 11/1992 | Pinchuk . |
| 5,195,984 | 3/1993 | Schatz . |
| 5,197,978 | 3/1993 | Hess . |
| 5,213,561 | 5/1993 | Weinstein et al. . |
| 5,222,969 | 6/1993 | Gillis . |
| 5,222,971 | 6/1993 | Willard et al. . |
| 5,234,457 | 8/1993 | Anderson . |
| 5,258,042 | 11/1993 | Mehta . |
| 5,266,073 | 11/1993 | Wall . |
| 5,282,823 | 2/1994 | Schwartz et al. . |
| 5,282,824 | 2/1994 | Gianturco . |
| 5,287,861 | 2/1994 | Wilk . |
| 5,292,331 | 3/1994 | Boneau . |
| 5,304,121 | 4/1994 | Sahatjian . |
| 5,306,294 | 4/1994 | Winston et al. . |
| 5,314,472 | 5/1994 | Fontaine . |
| 5,334,201 | 8/1994 | Cowan . |
| 5,336,518 | 8/1994 | Narayanan et al. . |
| 5,342,348 | 8/1994 | Kaplan . |
| 5,344,426 | 9/1994 | Lau et al. . |
| 5,360,401 | 11/1994 | Turnland . |
| 5,368,566 | 11/1994 | Crocker . |
| 5,370,691 | 12/1994 | Samson . |
| 5,383,892 * | 1/1995 | Cardom et al. .................... 606/198 |
| 5,383,928 | 1/1995 | Scott et al. . |
| 5,389,106 | 2/1995 | Tower . |
| 5,391,172 | 2/1995 | Williams et al. . |
| 5,397,355 | 3/1995 | Marin et al. . |
| 5,403,341 | 4/1995 | Solar . |
| 5,421,955 | 6/1995 | Lau et al. . |
| 5,423,885 | 6/1995 | Williams . |
| 5,433,706 | 7/1995 | Abiuso . |
| 5,437,632 | 8/1995 | Engelson . |
| 5,439,444 | 8/1995 | Anderson et al. . |
| 5,439,445 | 8/1995 | Kontos . |
| 5,443,500 | 8/1995 | Sigwart . |
| 5,449,373 * | 9/1995 | Pinchasik et al. .................... 606/198 |
| 5,480,423 | 1/1996 | Ravenscroft et al. . |
| 5,591,197 * | 1/1997 | Orth et al. ................ 623/1 |
| 5,697,971 * | 12/1997 | Fischell et al. ........... 623/12 |
| 5,733,303 * | 3/1998 | Israel et al. ............... 623/1 |
| 5,746,691 * | 5/1998 | Frantzen ................... 623/1 |
| 5,755,781 * | 5/1998 | Jayaraman ................ 623/1 |
| 5,776,161 * | 7/1998 | Globerman ................ 623/1 |
| 5,776,183 * | 7/1998 | Kanesaka et al. .......... 606/195 |

\* cited by examiner

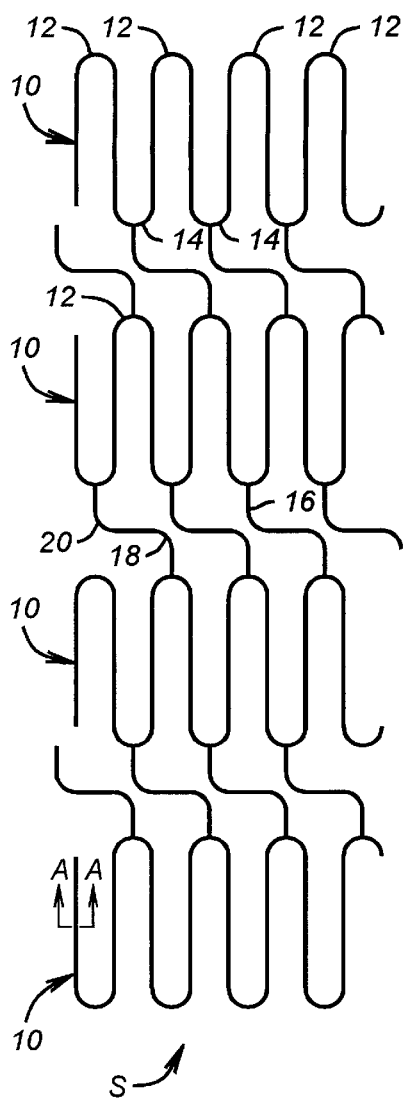
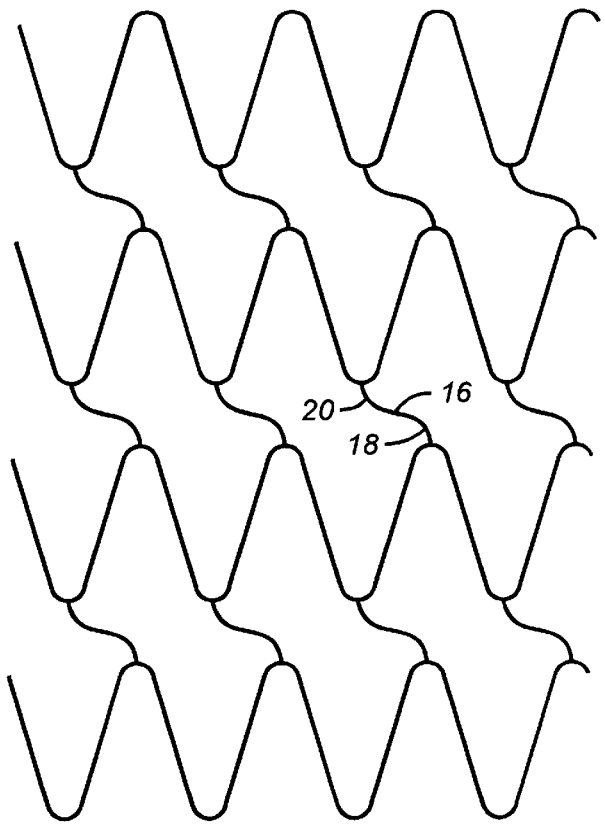
FIG. 1
FIG. 2
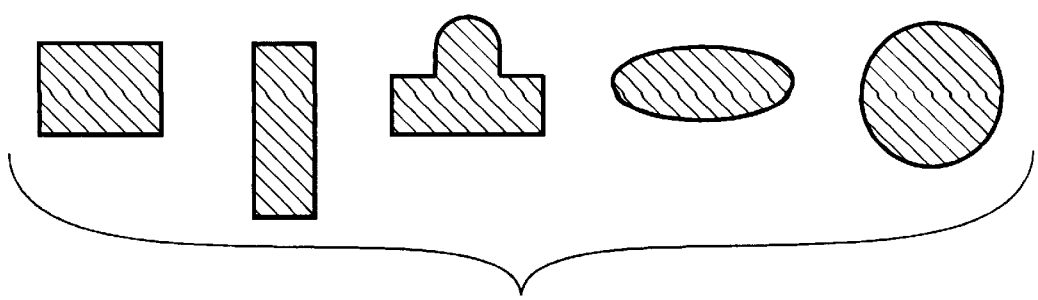
FIG. 3

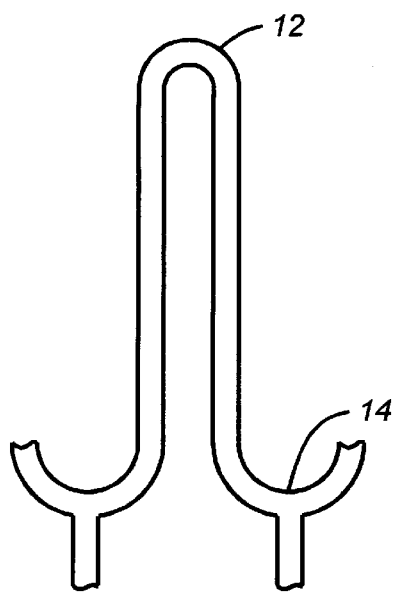
FIG. 4
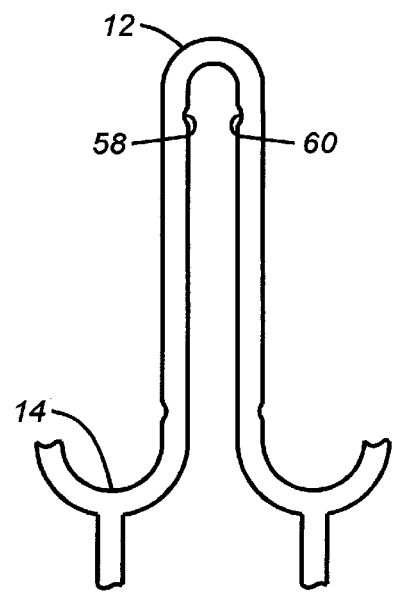
FIG. 5
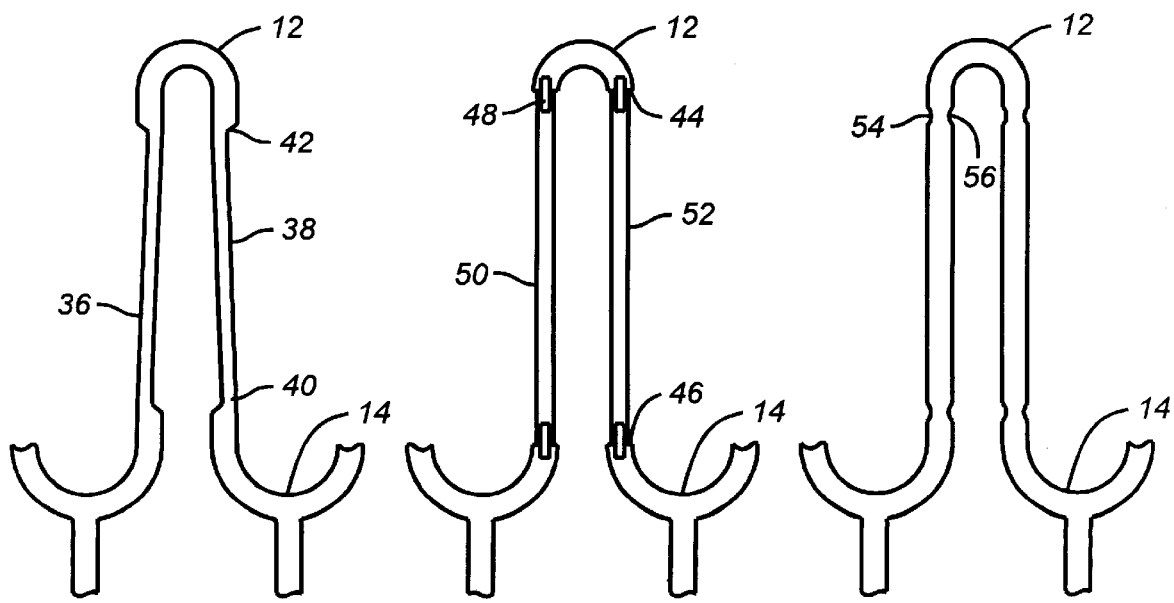
FIG. 6   FIG. 7   FIG. 8

FLEXIBLE STENT

This application is a continuation of copending application Ser. No. 08/582,657, filed on Jan. 4, 1996.

FIELD OF THE INVENTION

The field of this invention relates to vascular stents that can be delivered to a predetermined position and allowed to spring outwardly or, in the alternative, which can be expanded in place.

BACKGROUND OF THE INVENTION

Vascular stents are structures that are designed to maintain the patency of a vessel in the body. The stent provides internal support to allow the circulation to proceed therethrough. Stents can be used in the vascular system in ureters, bile ducts, esophagus, and in many other tubular structures in the human body.

Stents can be tubular or can be made from wire. Stents are typically made from a metal or polymeric substance or a metal coated with polymers which are biocompatible or contain heparin to reduce blood clotting or other tissue reactions. Many prior designs have used a coil approach where a wire is helically wound on a mandrel. Yet other designs have evolved—braided wire mesh and angulated wire forms wrapped on a spindle to form a coil.

U.S. Pat. No. 5,292,331 by Boneau and U.S. Pat. No. 5,403,341 describe such wire forms. These devices have very poor radial support to withstand the hoop strengths of the artery or vein and further are not suitable for arteries that are bent or curved or for long lesions; multiple stents are required. These designs do not provide any support to hold the wall of the artery, other than the memory of the metal.

Wall Stent, produced by Pfizer Inc., is a braided wire tube. Although this stent is flexible so as to be placed in curved arteries or veins and other body cavities, it does not have any radial strength imparted to it by design.

Wiktor, U.S. Pat. No. 4,649,922; 4,886,062; 4,969,458; and 5,133,732 describe a wire form stent. He describes stents made of wire helix made of a preformed wire which is in the sinusoidal form, in which either all or some of the adjacent strands are connected.

Arthus Fontaine, U.S. Pat. No. 5,370,683, also describes a similar device where a flat wire form of sinusoidal shape is wound on a mandrel to form a helical coil. the wire bends are "U" shaped and are connected to alternate "U"-shaped bands.

Allen Tower, U.S. Pat. Nos. 5,217,483 and 5,389,106 describes a similar device where the wire is preformed to a sinusoidal shape and subsequently wound on a mandrel to form a helical coil.

All of the above-described art fails to provide radial support. The pre-shaped wire form (sinusoidal in most of the prior art) is wrapped on a mandrel to form a coil. However, the forces imported by the vessel wall's hoop strength is radially inward. In other words, the force is acting perpendicular to the plane of the U-shaped wire form. This means that the bends that are in the wire add no structural strength to the wire form to support the force produced by the wall, which is radially inward.

When we examine the simple coils, such as taught in Scott U.S. Pat. No. 5,383,928 or Gene Samson U.S. Pat. No. 5,370,691 or Rolando Gills U.S. Pat. No. 5,222,969, it is apparent that the spring coil will withstand substantial radial forces due to the vessel wall; however, all these stents are bulky in their pre-expanded form and are hard to place in small and curved arteries or veins of the body. Also, a major disadvantage of this design is that when the coil stent is placed in a curved artery or vein, it forms an "accordion" shape whereby some strands in the outer radius are spread and those of the inner radius are gathered. Spring coils can also "flip" to form a flat structure when a longitudinal force is applied on one side of the stent.

The other types of stents that have been developed are tube stents. Palmer, U.S. Pat. No. 4,733,665; 4,739,762; 7,776,337; and 4,793,348 describe such a tube stent of slotted metal tube. The slotted metal tube is expanded by a high-pressure balloon to implant the stent into the inside wall of the artery or vein.

Joseph Weinstein, U.S. Pat. No. 5,213,561 describes a similar stent made of tubular materials with slots cut into it. On expansion using a balloon, it forms a structure with diamond-shaped slots.

Henry Wall, U.S. Pat. No. 5,266,073 also describes a stent, tubular, that has slots machined into it. When expanded, the edges of the stent lock to form a cylinder. Not only is this device stiff and can only be used for short lesions, but also the diameter cannot be adjusted to meet the exact needs of the particular vessel but it is fixed to the predetermined sizes.

Lau and Hastigan, U.S. Pat. No. 5,344,426 describes a slotted tubular stent that has a structure similar to Henry Wall's but has provided prongs that will lock in as the stent is expanded.

Michael Marin, U.S. Pat. No. 5,397,355 also describes a tubular slotted stent with locking prongs.

U.S. Pat. No. 5,443,500 illustrates the use of square openings with rectangular prongs that stick therethrough to lock the stent. This design, as well as other locking mechanisms, generally have resulted in very stiff stents because of the use of a tubular-type grid construction. Further, the locking devices have resulted in sharp outwardly oriented tabs which are used for the locking, which could cause vascular damage.

All the above-described tube stents, although typically providing substantial radial support when expanded, are not flexible enough to be placed in curved vessels. Arteries and veins in the human body are mostly curved and are tapered. As such, these tube stents suffer from this main disadvantage.

European patent document 042172982 employs wires that are doubled up and whose ends are snipped off to make a given joint. Such doubling up at the junction of two elements with snipped off free ends creates a potential puncture problem upon radial expansion. The sheer bulk of the doubled up wires makes them rotate radially outwardly away from the longitudinal centerline of the stent, while the plain ends on such an arrangement which are snipped off offer the potential of sharp points which can puncture or damage the intima. On the other hand, the apparatus of the present invention, employing sharp angles, as defined, avoids this problem in an embodiment which illustrates a continuous wire or wire-like member bent into a sharp angle. This type of structure alleviates the concerns of sharp edges, as well as the tendency of a doubled up heavy joint to rotate outwardly toward the intima upon radial expansion of the stem, as would be expected in the EPO reference 042172982.

Often these stents are layered with polymeric sheaths that are impregnated with biocompatible substances or can be coated with heparin or hydrogel. Most sheath-type coatings reduce endothelial cell growth through the stent, which is a major requirement in successful stenting of body cavities such as arteries and veins.

Several parameters in design of stents are important. Of the more important parameters is the issue of recoil. Recoil deals with the memory of the stent material which, generally speaking, upon expansion in the blood vessel will want to recoil back to its original shape. This can be problematic because it is desirable for the stent, once expanded, to remain in good contact with the vessel wall to avoid longitudinal shifting. Furthermore, any recoil constricts the flow passage and presents a greater portion of the stent in the blood flowpath, thus creating additional complications due to the turbulence which ensues.

Related to the concern regarding recoil is another concern regarding component twist. This phenomenon generally occurs when the cross-sectional area of the components is rectangular, such as when the stent is manufactured from a cylindrical piece which is then cut by lasers or other means to form the particular pattern. Particularly in the honeycombed designs involving the use of square or rectangular element cross-sections, radial expansion of such stents generally results in a twist of the component segments such that they extend into the flowpath in the artery or vein. Again, this causes turbulence which is undesirable.

Related to the problem of recoil or constriction after expansion is the ability of the stent to anchor itself in the vascular wall. An anchoring system that does not cause trauma is a desirable feature not found in the prior art.

Yet other considerations which are desirable in a stent not found in the prior art is the flexibility to be maneuvered around bends in the vascular system, coupled with the ability to conform to a bend without kinking or leaving large open areas. The stents of the present invention have the objective of addressing the issue of recoil, as well as providing an anchoring mechanism to fixate the stent once set. Several of the designs incorporate flexibility to allow the stent to follow a bend or curve in a vascular flowpath while a the same time providing sufficient radial deformation to ensure proper fixation while minimizing angular twisting movements of the stent components to minimize turbulence through the stent.

In a recent article appearing in late 1995, by Dr. Donald S. Baim, entitled "New Stent Designs," a description is given of the ideal endovascular prosthesis. There, Dr. Baim indicates that the ideal stent should have low implantation profile with enhanced flexibility to facilitate delivery. He goes on to say that the stent should be constructed from a noncorrosive, nonthrombogenic radiopaque alloy and have expanded geometry which maximizes radial strength to resist vascular recoil. The ideal stent described by Baim is further described as having a wide range of diameters and lengths. Dr. Baim concludes that it is unlikely that any current designs satisfy all these requirements. Thus, one of the objectives of the present invention is to go further than the prior designs in satisfying the criteria for the ideal designs as set forth by Dr. Baim in his recent article.

SUMMARY OF THE INVENTION

A stent is disclosed which comprises generally of ring having, in the preferred embodiment, crossties that have flexibility by having at least one bend. The rings themselves have predetermined stress-relieving points to predispose, by stress relief, particular segments of each ring to bend upon application of an expansion force such as by a balloon or by other means. In the preferred embodiment, the individual rings have notches, reducing the cross-sectional areas at particular locations adjacent reversing bends such that upon radial expansion, bending occurs at these reduced cross-sectional areas to prevent stress from accumulating at the reversing bends.

BRIEF DESCRIPTION OF THE DRAWINGS

FIG. 1 illustrates the stent of the present invention in an unrolled condition prior to expansion.

FIG. 2 is the stent shown in FIG. 1 in an unrolled condition after expansion.

FIG. 3 is a section along lines A—A of FIG. 1 and illustrates several different cross-sectional shapes that can be used for the stent illustrated in FIG. 1.

FIG. 4 is a detailed view of the stent in FIG. 1, shown without any cross-sectional changes to the undulating design of the ring structure illustrated in FIG. 1.

FIG. 5 is similar to FIG. 4 except that it employs singular notches adjacent reversing bends.

FIG. 6 employs a change in the cross-sectional shape taking place adjacent each reversing bend.

FIG. 7 illustrates a joint involving a transverse tab adjacent the reversing bends.

FIG. 8 involves opposed notches on each side of the wire adjacent a reversing bend.

DETAILED DESCRIPTION OF THE PREFERRED EMBODIMENT

Figure 10:
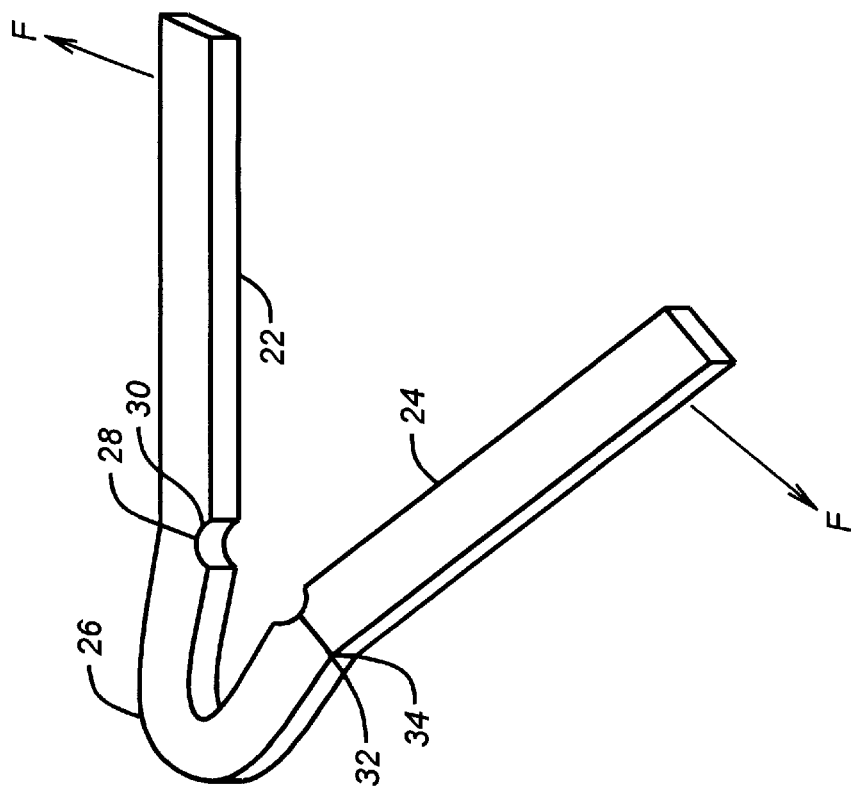
FIG. 10 illustrates the action upon radial expansion using a notch and its effect on the reversing bend.

FIG. 1 shows, in flattened out form, a stent S which is unrolled along its longitudinal axis. The stent S has a series of rings 10 which are preferably of a wire material (preferably stainless steel, nickel-titanium alloys, tantalum alloys) bent in a series of reversing undulations 12 and 14. The wire can be coated with polymer such as polyethylene, polytetrafluoroethylene (Teflon®), or polylactates containing heparin or drugs or radioactive material. The bends 12 may have a similar radius or may vary as among bends 12 or as among bends 14. In other words, each of the bends 12 may be identical to each other. Each of the bends 14 may be identical to each other. Each bend 12 may be identical to each bend 14. One bend 12 can be different from another bend 12, which is in turn also different from another bend 14, or any combinations of the above. While rounded bends are shown as 12 and 14, other shapes can be used to create a generally undulating pattern, such as sharp bends which generally form a V-shape. Connecting each row 10 is one or more crossties 16. In the preferred embodiment, the crossties 16 have flexibility in that they have at least one bend 18, while a double bend, such as including 18 and 20, is preferred for the construction of the crossties 16. One or more crossties can be used which connect a bend 14 to its opposing bend 12. Thus, as shown in FIG. 1, the crossties 16, looking from bottom to top, make a bend to the left and a bend to the right on their way from reverse bend 12 to a reverse bend 14. One or more crossties 16 can be used between rings 10 up to a maximum where every reversing bend, such as 14, is connected to an adjacent but offset circumferentially reversing bend 12.

FIG. 2 illustrates the stent S in a radially expanded form, illustrating that the crossties 16 continue to retain flexibility because of the reversing bends 18 and 20. Thus, the longitudinal flexibility of the stent S is retained, even in the expanded position. The use of the crossties with, at minimum, a single bend gives them flexibility. The design involving rings 10 connected by crossties 16 prevents stiffness experienced in some prior designs that had a particular longitudinal segment with undue stiffness giving the stent S a "backbone," thus making it unduly stiff longitudinally. Use of the flexible crossties 16 also provides flexibility for relative rotation between rings 10 while the expansion is taking place. Flexibility is also provided in the longitudinal direction as the crossties 16 may elongate in that direction without putting the stent S into a kink or a longitudinal bind.

FIG. 3 illustrates alternative cross-sectional shapes for the wire cross-section which makes up each of the rings 10 and/or the crossties 16. Thus, FIG. 3 illustrates squares, rectangles, circles, ovals, and composite shapes.

Figure 9:
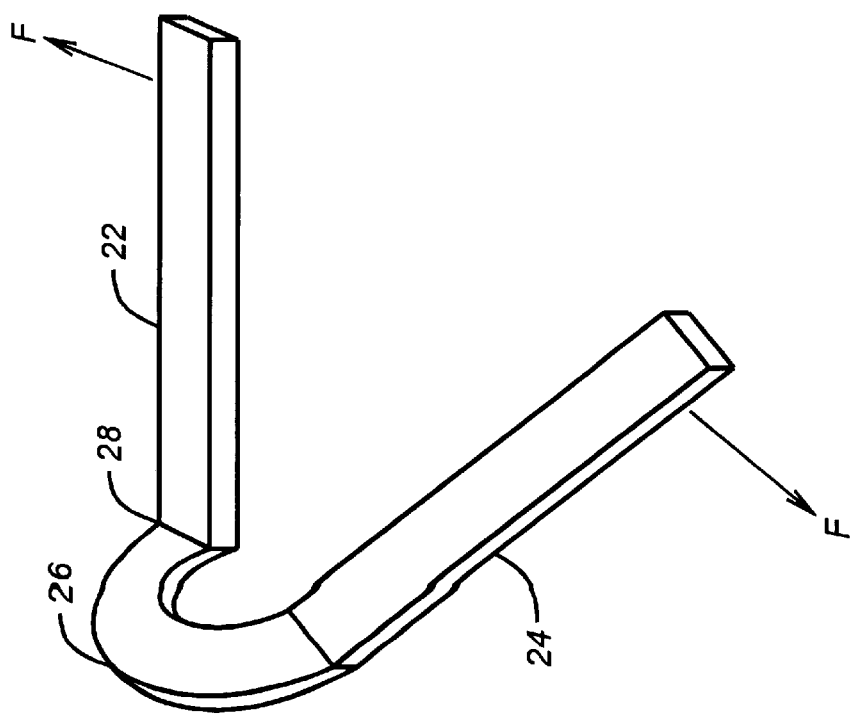
FIG. 9 illustrates what occurs on radial expansion of each of the rings without the use of a stress-relief mechanism such as a notch or a cut-out.

One of the concerns with an undulating structure, such as illustrated in FIG. 1, is the reversing bends 12 or 14, unless some provisions are made, experience undue stress and are even prone to bending out of their plane when the stent is radially expanded. This phenomenon is illustrated in FIG. 9. There, a pair of straight segments 22 and 24 are joined together by a reversing bend 26. As illustrated in FIG. 9, the cross-sectional area of the segments 22 and 24 are rectangular, one of the shapes shown in FIG. 3. It should be noted that other cross-sections, apart those illustrated in FIG. 3, can be used without departing from the spirit of the invention.

With no significant cross-sectional change occurring at the transition or near the transition 28 between the reverse bend 26 and the segments 24 or 22, the stress is transferred to the reverse bend 26 when an expansion force F tries to radially expand the stent S by moving segments 22 and 24 apart. Depending on the amount of stress induced, a bending occurs, as shown in FIG. 9, where the reverse bend 26 bends out of plane so that it is no longer in alignment with the segments 22 and 24, which was its condition prior to the application of force F.

FIG. 10 shows the contrast of the behavior of the reverse bend 26 when a notch 30 is placed adjacent the transition 28 between the reverse bend 26 and the segment 22 and a similar notch 32 is placed near transition 34 between the reverse bend 26 and the segment 24. What results is a reduced cross-sectional area at transitions 28 and 34. Thus, when force F is applied to the segments 22 and 24, there is a permanent bending occurring at the zone of least cross-sectional area, i.e., transitions 28 and 34, with their respective notches 30 and 32. Accordingly, the stress from radial expansion of a ring 10 as illustrated in FIG. 1 is absorbed by a bending or deformation at the transitions 28 and 32, thus minimizing if not eliminating the applied stress to the reverse bend 26 after radial expansion of the stent S by expanding all of the rings 10. This type of structure illustrated in FIG. 10 can be employed in the unrolled stent shown in FIGS. 1 and 2.

Other alternative mechanisms for reducing the stress at the reverse bend are illustrated in FIGS. 5–8. It should be noted that the features illustrated in FIGS. 5–8 are to be found in the stent shown in FIGS. 1 and 2; however, in order to show the overall layout of the stent S, FIGS. 1 and 2 are not sufficiently magnified so that these details can be seen. However, FIGS. 5–8 represent a greater magnification of adjacent reverse bends, such as 12 and 14.

In FIG. 6, the connecting segments 36 and 38 have a smaller cross-sectional area than the cross-sectional area at the reverse bends 12 and 14, thus creating zones of transition of cross-section 40 adjacent reverse bend 14 and 42 adjacent reverse bend 12. This construction is typical for each of the rings 10 of a particular stent. It should be noted that the various features illustrated in FIGS. 5–8 can be used uniformly throughout the stent or mixed and matched for a desired effect.

The detail in FIG. 7 illustrates a cross-sectional area transition point 44 and 46, respectively adjacent reverse bends 12 and 14. Here, there is not only a transition cross-sectional area but transverse tabs 48 are used to secure the joint between segments 50 and 52, which have a smaller cross-sectional area than the cross-sectional area of reverse bends 12 and 14.

FIG. 8 illustrates the use of opposed notches 54 and 56 adjacent the entrance and exit to each reverse bend 12 and 14. FIG. 5 illustrates the use of similar notches 58 and 60 at the entrance and exit of each reverse bend 12 and 14. The difference between FIG. 5 and FIG. 8 is that in FIG. 8, the notches 54 and 56 oppose each other at the entrance and exit of each reverse bend 12 or 14, while in FIG. 5 the notches can be interiorly located, as shown in FIG. 5, or in the alternative, exteriorly located at the entrance and exit to each reverse bend 12 and 14. It should be noted that the changes in cross-sectional area do not need to be literally at the point of transition between the rounded portion of a reverse bend 12 or 14 and the straight segment which adjoins the reverse bends. However, the preferred location is at that transition. Locating the cross-sectional area change before entering the transition from the straight segment to the curved segment is also possible, depending on the degree of stress relief desired.

Figure 11:
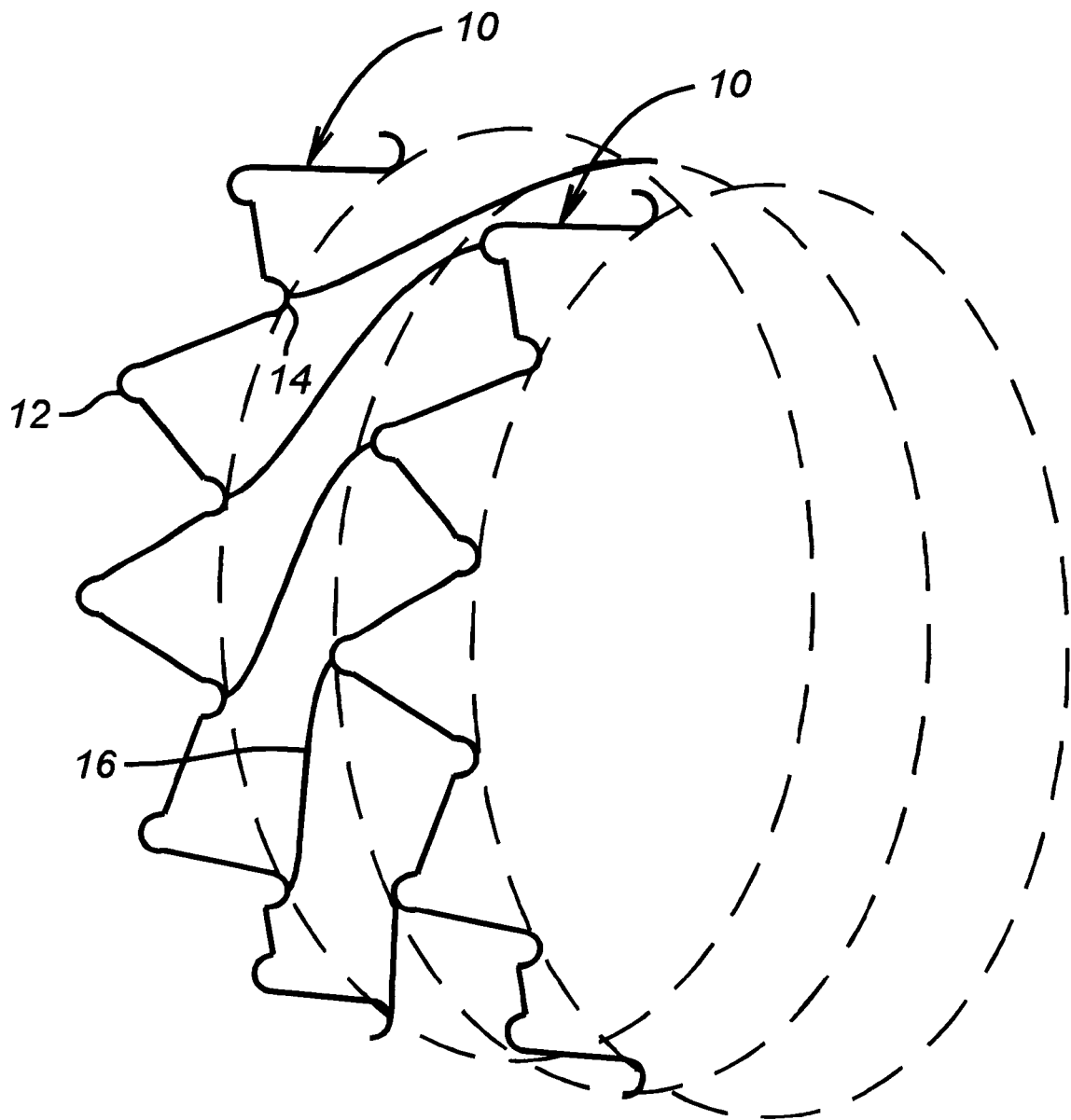
FIG. 11 is a perspective view of the stent shown in FIG. 2 in the expanded position.

FIG. 11 illustrates the stent S shown in unrolled form in FIGS. 1 and 2 in a perspective view after radial expansion. It should be noted that the crossties 16 retain their flexibility, even after expansion, and that the reverse bends 12 and 14 have not buckled out of the cylindrical surface defined by the expanded stent S shown in FIG. 11. The buckling feature, which can occur in prior designs without the stress relief mechanism, is illustrated in FIG. 9.

FIG. 4 illustrates that it is within the purview of the invention to use a plurality of rings 10 connected by flexible crossties 16 without the change in cross-sectional area occurring at the reverse bends 12 and 14. While the embodiments in FIGS. 5–8 are preferred, it is within the purview of the invention to provide a stent with a multiplicity of rows 10 of undulating wire components which are connected by one or more crossties 16, each of which have at least one bend so that upon radial expansion into the position shown in FIGS. 2 and 11, the crossties 16 continue to retain flexibility in at least one but preferably more directions. Thus, the individual rings 10 have longitudinal flexibility and may rotate to some degree with respect to each other, all to conform to the tortuous path in which the stent S may be placed. By adding the change in the cross-sectional area feature, as shown in FIGS. 5–8, by using one or more of those features in a single stent, a stent is produced that is flexible, yet when expanded, retains its flexibility and is not subjected to stress to a significant degree at reversing bends after complete radial expansion. By focusing the stress occurring during radial expansion to a particular point outside the reversing bend, a simple-to-make construction occurs which addresses the concerns of some of the prior art designs which have tackled this problem by using varying degrees of curvature, such as European application No.

0662307, assigned to Advanced Cardiovascular Systems. This design, with the flexible crossties 16, represents a considerably more flexible design than rolled up coil springs such as that illustrated in U.S. Pat. No. 4,969,458. Crossties which are essentially straight, such as those illustrated in U.S. Pat. No. 5,421,955, do not afford the flexibility realized by the stent S of the present invention. It should be noted that as more bulk is presented at the transition between segments such as 22 and 24 in FIG. 9, the more likely is the bending to occur when subjected to radial expansion, as illustrated schematically by force F. Thus, designs that use doubled up wires at the apex, such as European application No. 0421729, assigned to Medtronic, exacerbate the bending results shown in FIG. 9, as well as increasing the stiffness of the stent and the force necessary for radial expansion of each of its individual rings. Additionally, by use of crossties which are coiled springs which protrude out of the cylindrical surface defined by the stent S, additional complications are created since the crossties will intrude into the vascular wall, creating additional irritation to the patient or worse damage if there is penetration of the vascular wall.

Accordingly, the above-described stent S of the present invention has the advantages of flexibility in view of the unique crossties which are used. The crossties remain in the cylindrical surface defined by the shape of the stent S, even upon radial expansion. The crossties 16 retain their flexibility, even after full radial expansion occurs. By use of the cross-sectional area changes, the applied stresses from radial expansion are focused to this transition zone as opposed to other places, such as the return bends. By focusing the deformation to the transition zone, stress is minimized or reduced in the reverse bend section, such as 12 or 14, and further the tendency of the reverse bends such as 12 or 14 to protrude out of the cylindrical surface defined by the stent S is greatly reduced, if not eliminated.

The foregoing disclosure and description of the invention are illustrative and explanatory thereof, and various changes in the size, shape and materials, as well as in the details of the illustrated construction, may be made without departing from the spirit of the invention.

What is claimed is:

1. A stent comprising:

a plurality of rings arranged in general alignment to define a cylindrical shape, each ring comprises a singular elongated wire member having discrete reversing bends which do not intersect with other reversing bends and at least two cross-sectional areas identified by at least one cross-sectional change location, said wire member forming an undulating pattern;

at least one crosstie connecting adjacent rings said crosstie disposed in general alignment with a longitudinal axis defined by said rings, said crosstie having at least one bend formed therein;

the cross-sectional area of said wire member changes adjacent at least one of said reversing bends;

said wire member which comprises each said rings, when expanded radially outwardly, bends at said cross-sectional change location adjacent said reversing bends; and said reversing bends remain generally aligned to said cylindrical shape defined by said rings after radial expansion due to bending at said cross-sectional change locations.

2. A stent, comprising:

a plurality of rings arranged in general alignment to define a cylindrical shape, each ring comprises a singular elongated wire member having discrete reversing bends which do not intersect with other reversing bends, and at least two cross-sectional areas defined by at least one cross-sectional change location, said wire member forming an undulating pattern;

at least one crosstie connecting adjacent rings said crosstie disposed in general alignment with a longitudinal axis defined by said rings, said crosstie having at least one bend formed therein;

said wire member having at least one straight section between said reversing bends;

the cross sectional area of said wire member changes in said straight section and adjacent said reversing bends;

said wire member which comprises each said rings, when expanded radially outwardly, bends at said cross-sectional change location adjacent said reversing bends; and said reversing bends remain generally aligned to said cylindrical shape defined by said rings after radial expansion due to bending at said cross-sectional change locations.

3. A stent, comprising:

a plurality of rings arranged in general alignment to define a cylindrical shape, each ring comprises a singular elongated wire member having discrete reversing bends which do not intersect with other reversing bends, said wire member forming an undulating pattern, said wire member having at least one cross-sectional area;

at least one crosstie connecting adjacent rings said crosstie disposed in general alignment with a longitudinal axis defined by said rings, said crosstie having at least one bend formed therein;

the wire member is formed having a notch wherein the cross-sectional area of the wire member changes at a notch location;

said notch is located adjacent at least one of said reversing bends.

4. The stent of claim 3, wherein:

said change in cross-section is accomplished by opposed notches.

5. A stent, comprising:

a plurality of rings arranged in general alignment to define a cylindrical shape, each ring comprises a singular elongated wire member having reversing bends forming an undulating pattern;

at least one crosstie connecting adjacent rings wherein said crosstie is disposed in general alignment with a longitudinal axis defined by said rings; and said wire member is formed having a notch adjacent at least one of said reversing bends which defines a change in cross-sectional area.

6. The stent of claim 5, wherein:

said change in cross-sectional area is accomplished by opposed notches.

7. A stent, comprising:

a plurality of rings arranged in general alignment to define a cylindrical shape, each ring comprises a singular elongated wire member having discrete reversing bends which do not intersect with other reversing bends, said wire member forming an undulating pattern; and having at least two cross-sectional areas identified by at least one cross-sectional change location; and at least one cross-tie having said connecting adjacent rings said crosstie disposed in general alignment with a longitudinal axis defined by said rings, said crosstie having at least one bend formed between said ends to allow said crosstie to flex as said rings expand while remaining within the confines of said cylindrical shape; and the cross-sectional area of said wire member changes adjacent at least one of said reversing bends.

8. The stent of claim 7, wherein:

said wire member changes cross-section adjacent each said reversing bend.

9. The stent of claim 8, wherein:

said wire member changes cross-section on both sides of each said reversing bend.

10. The stent of claim 7, wherein:

said wire member which comprises said rings, when said rings are expanded radially outwardly, bends at said cross-sectional change location adjacent said reversing bends.

11. The stent of claim 1, further comprising:

a plurality of non-overlapping crossties each having at least two bends.

12. The stent of claim 11, wherein:

said bends define at least two slope changes in said crossties.

13. The stent of claim 12, wherein:

each crosstie connects a reversing bend in one of said rings to the next adjacent circumferentially offset reversing bend on an adjacent ring.

14. The stent of claim 1, wherein:

said at least one crosstie comprises at least two reversing bends located remotely from said end of said crosstie.

15. The stent of claim 7 wherein:

said at least one crosstie comprises at least two reversing bends located remotely from said ends of said crosstie; and said bends define a turn of no less than about 90°.

16. The stent of claim 15, wherein:

said crosstie having a first end offset circumferentially from a second end.

17. The stent of claim 15, wherein that portion of said crossties extending between said first and second ends and up to said bends of said crosstie are in substantial longitudinal alignment with the longitudinal axis of said cylindrical shape.

18. The stent of claim 3, wherein:

said wire-like member has straight sections between said reversing bends;

said straight sections have a smaller cross-sectional area than the cross-sectional area through said reversing bends.

19. A stent, comprising:

a plurality of rings arranged in general alignment to define a cylindrical shape, each ring comprises a singular elongated wire member having discrete reversing bends which do not intersect with other reversing bends; said wire member forming an undulating pattern and having at least one cross-section;

at least one crosstie connecting adjacent rings said crosstie disposed in general alignment with a longitudinal axis defined by said rings, said crosstie having at least one bend formed therein; and said wire member having at least one straight section between said reversing bends;

the cross-section of said wire member changes in said straight section and adjacent said reversing bends.

20. The stent of claim 9, wherein:

said straight section has a smaller cross-sectional area than the cross-sectional area through an adjacent said reverse bend.

21. The stent of claim 19, wherein:

said wire member changes cross-section adjacent each said reversing bend.

22. The stent of claim 19, wherein:

said wire member changes cross-section on both sides of each said reversing bend.

23. The stent of claim 19, wherein:

said wire member which comprises said rings, when said rings are expanded radially outwardly, bends at said cross-sectional change location adjacent said reversing bends.

24. A stent of claim 19, further comprising:

a plurality of non-overlapping crossties each having at least two bends.

25. The stent of claim 24, wherein:

said bends define at least two slope changes in said crossties.

26. The stent of claim 25, wherein:

each crosstie connects a reversing bend in one of said rings to the next adjacent circumferentially offset reversing bend on an adjacent ring.

* * * * *